(12) United States Patent
Govari

(10) Patent No.: US 7,321,228 B2
(45) Date of Patent: Jan. 22, 2008

(54) DETECTION OF METAL DISTURBANCE IN A MAGNETIC TRACKING SYSTEM

(75) Inventor: Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 101 days.

(21) Appl. No.: 10/632,217

(22) Filed: Jul. 31, 2003

(65) Prior Publication Data

US 2005/0024043 A1 Feb. 3, 2005

(51) Int. Cl.
G01B 7/30 (2006.01)
G01C 17/38 (2006.01)

(52) U.S. Cl. .......................... 324/207.17; 324/207.12; 702/95; 702/150

(58) Field of Classification Search .......... 324/207.17, 324/207.12; 600/424; 702/153, 94, 95, 702/150, 152
See application file for complete search history.

(56) References Cited

U.S. PATENT DOCUMENTS

| | | | |
|---|---|---|---|
| 3,644,825 A | 2/1972 | Davis Jr. et al. ............... 324/41 |
| 3,868,565 A | 2/1975 | Kuipers .................... 324/34 R |
| 4,017,858 A | 4/1977 | Kuipers .................. 343/100 R |
| 4,054,881 A | 10/1977 | Raab ....................... 343/112 R |
| 4,173,228 A | 11/1979 | Van Steenwyck et al. |
| 4,287,809 A | 9/1981 | Egli et al. .................. 89/41 EA |
| 4,309,697 A | 1/1982 | Weaver |
| 4,317,078 A | 2/1982 | Weed et al. ................. 324/208 |
| 4,416,289 A | 11/1983 | Bresler ........................ 128/737 |
| 4,526,177 A | 7/1985 | Rudy et al. .................. 128/737 |
| 4,560,930 A | 12/1985 | Kouno ........................ 324/207 |
| 4,605,897 A | 8/1986 | Gelinas |
| 4,613,866 A | 9/1986 | Blood ......................... 343/448 |
| 4,622,542 A | 11/1986 | Weaver |
| 4,642,786 A | 2/1987 | Hansen ....................... 364/559 |
| 4,651,436 A | 3/1987 | Gaal ........................... 33/533 |
| 4,710,708 A | 12/1987 | Rorden et al. .............. 324/207 |
| 4,771,237 A | 9/1988 | Daley |
| 4,791,412 A | 12/1988 | Brooks |
| 4,849,692 A | 7/1989 | Blood |

(Continued)

FOREIGN PATENT DOCUMENTS

EP 894473 A2 2/1999

(Continued)

OTHER PUBLICATIONS

Schaum's Outline Of Theory And Problems Of Analog and Digital Communications, Hwei P. Hsu PhD, 1993, p. 58.*

(Continued)

*Primary Examiner*—Patrick Assouad
*Assistant Examiner*—David M Schindler
(74) *Attorney, Agent, or Firm*—Louis J. Capezzuto

(57) ABSTRACT

A method for tracking an object includes producing energy fields at a plurality of different frequencies in a vicinity of the object, and receiving signals that are generated at a location of the object at the different frequencies in response to the energy fields. Multiple computations are made of spatial coordinates of the object based on the signals received at the different frequencies. Convergence of the computations is tested in order to ascertain whether the energy fields have been perturbed by an article in the vicinity of the object.

22 Claims, 2 Drawing Sheets

U.S. PATENT DOCUMENTS

| | | | |
|---|---|---|---|
| 4,868,504 A | 9/1989 | Johnson | |
| 4,905,698 A | 3/1990 | Strohl, Jr. et al. | |
| 4,931,730 A | 6/1990 | Olsen | |
| 4,945,305 A | 7/1990 | Blood | |
| 5,002,137 A | 3/1991 | Dickinson et al. | 175/19 |
| 5,008,649 A | 4/1991 | Klein | |
| 5,028,869 A | 7/1991 | Dobmann | |
| 5,042,486 A | 8/1991 | Pfeiler et al. | 128/653 R |
| 5,057,095 A | 10/1991 | Fabian | |
| 5,068,608 A | 11/1991 | Clark, Jr. | 324/220 |
| 5,099,845 A | 3/1992 | Besz et al. | |
| 5,172,056 A | 12/1992 | Voisin | 324/207.17 |
| 5,211,165 A | 5/1993 | Dumoulin et al. | 128/653.1 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,274,328 A | 12/1993 | Begin et al. | |
| 5,309,913 A | 5/1994 | Kormos et al. | 128/653.1 |
| 5,325,873 A | 7/1994 | Hirschi et al. | |
| 5,375,596 A | 12/1994 | Twiss et al. | 128/653.1 |
| 5,377,678 A | 1/1995 | Dumoulin et al. | 128/653.1 |
| 5,391,199 A | 2/1995 | Ben-Haim | 607/122 |
| 5,425,367 A | 6/1995 | Shapiro et al. | |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | |
| 5,453,687 A | 9/1995 | Zierdt et al. | 324/207.17 |
| 5,506,506 A | 4/1996 | Candy | |
| 5,519,317 A | 5/1996 | Guichard | |
| 5,534,873 A | 7/1996 | Weichman | |
| 5,553,611 A | 9/1996 | Budd et al. | |
| 5,558,091 A | 9/1996 | Acker et al. | |
| 5,577,502 A | 11/1996 | Darrow et al. | 128/653.1 |
| 5,600,330 A | 2/1997 | Blood | |
| 5,622,169 A | 4/1997 | Golden et al. | 128/653.1 |
| 5,629,621 A | 5/1997 | Goldfine et al. | |
| 5,644,229 A | 7/1997 | Dossel et al. | |
| 5,646,524 A | 7/1997 | Gilboa | 324/207.17 |
| 5,682,886 A | 11/1997 | Delp et al. | 128/653.1 |
| 5,694,945 A | 12/1997 | Ben-Haim | 128/736 |
| 5,715,822 A | 2/1998 | Watkins et al. | 128/653.5 |
| 5,729,129 A | 3/1998 | Acker et al. | 324/207.12 |
| 5,752,513 A | 5/1998 | Acker et al. | 128/653.1 |
| 5,767,669 A | 6/1998 | Hansen et al. | |
| 5,769,843 A | 6/1998 | Abela et al. | 606/10 |
| 5,797,849 A | 8/1998 | Vesely et al. | 600/461 |
| 5,831,260 A | 11/1998 | Hansen | |
| 5,847,976 A | 12/1998 | Lescourret | |
| 5,879,297 A | 3/1999 | Haynor et al. | 600/407 |
| 5,899,860 A | 5/1999 | Pfeiffer et al. | |
| 5,913,820 A | 6/1999 | Bladen et al. | |
| 5,967,980 A | 10/1999 | Ferre | |
| 5,997,473 A | 12/1999 | Taniguchi et al. | 600/117 |
| 6,073,043 A * | 6/2000 | Schneider | 600/424 |
| 6,122,538 A | 9/2000 | Sliwa, Jr. et al. | |
| 6,127,821 A | 10/2000 | Ramsden | |
| 6,147,480 A | 11/2000 | Osadchy et al. | |
| 6,150,810 A | 11/2000 | Roybal | |
| 6,172,499 B1 | 1/2001 | Ashe | |
| 6,177,792 B1 | 1/2001 | Govari | |
| 6,201,987 B1 | 3/2001 | Dumoulin | |
| 6,226,547 B1 | 5/2001 | Lockhart et al. | |
| 6,239,724 B1 | 5/2001 | Doron et al. | |
| 6,246,231 B1 | 6/2001 | Ashe | |
| 6,246,898 B1 | 6/2001 | Vesely | |
| 6,366,799 B1 | 4/2002 | Acker | |
| 6,369,564 B1 | 4/2002 | Khalfin et al. | |
| 6,373,240 B1 | 4/2002 | Govari | |
| 6,373,387 B1 | 4/2002 | Qiu | |
| 6,400,139 B1 | 6/2002 | Khalfin et al. | |
| 6,427,079 B1 | 7/2002 | Schneider et al. | |
| 6,443,894 B1 | 9/2002 | Sumanaweera | |
| 6,484,049 B1 | 11/2002 | Seeley | |
| 6,484,118 B1 | 11/2002 | Govari | |
| 6,493,573 B1 | 12/2002 | Martinelli et al. | |
| 6,498,477 B1 | 12/2002 | Govari et al. | |
| 6,690,963 B2 | 2/2004 | Ben-Haim et al. | |
| 6,774,624 B2 | 8/2004 | Anderson | |
| 6,788,967 B2 | 9/2004 | Ben-Haim | |
| 2001/0035815 A1 | 11/2001 | Fletcher | |
| 2002/0165448 A1 | 11/2002 | Ben Haim | |
| 2003/0135112 A1 | 7/2003 | Ritter et al. | |

FOREIGN PATENT DOCUMENTS

| | | |
|---|---|---|
| EP | 96/4261 A2 | 12/1999 |
| EP | 1174082 A1 | 1/2002 |
| EP | 1 203 560 A2 | 5/2002 |
| JP | 10094609 | 4/1998 |
| WO | WO 92/03090 | 3/1992 |
| WO | WO 94/04938 | 3/1994 |
| WO | WO 94/23647 | 10/1994 |
| WO | WO 96/05768 A1 | 2/1996 |
| WO | WO 96/41119 | 12/1996 |
| WO | WO 97/29678 | 8/1997 |
| WO | WO 97/29679 | 8/1997 |
| WO | WO 97/29709 | 8/1997 |
| WO | WO 97/29710 | 8/1997 |
| WO | WO 97/32179 | 9/1997 |
| WO | WO 97/42517 | 11/1997 |
| WO | WO 98/36236 | 8/1998 |
| WO | WO 99/32033 | 7/1999 |
| WO | WO 99/52430 | 10/1999 |

OTHER PUBLICATIONS

Iterative method, Wikipedia the free encyclopedia, http://en.wikipedia.org/wiki/Iterative_method, printed Oct. 16, 2006, 3 pages.*
U.S. Appl. No. 09/621,322 filed Jul. 20, 2000, Biosense, Inc.
U.S. Appl. No. 10/302,112, Biosense, Inc.
U.S. Appl. No. 10/448,289, Biosense, Inc.
U.S. Appl. No. 10/448,291, Biosense, Inc.
John David Jackson, "Classical Electrodynamics", Second Edition, John Wiley & Sons, New York, 1975, p. 178.
William H. Press et al., "Numberical Recipes in C, The Art of Scientific Computing", Second Edition, Cambridge University Press, ISBN 052143108, pp. 383-393.
European Search Report for EP 04 25 481 dated Nov. 5, 2004.
Feiste, K. L., Fetter Marques, P., Reichert, Ch., Reimche, W., Stegemann,D.: "Characterization of Nodular Cast Iron Properties by Harmonic Analysis of Eddy Current Signals" NDT.NET, [Online] vol. 3, No. 10, Oct. 1998 (Oct. 1998), XP002295053 Retrieved from the Internet: URL:http://www.ndt.net/article/ecndt98/nuc lear/245/245.htm> [retrieved on Sep. 03, 2004].

* cited by examiner

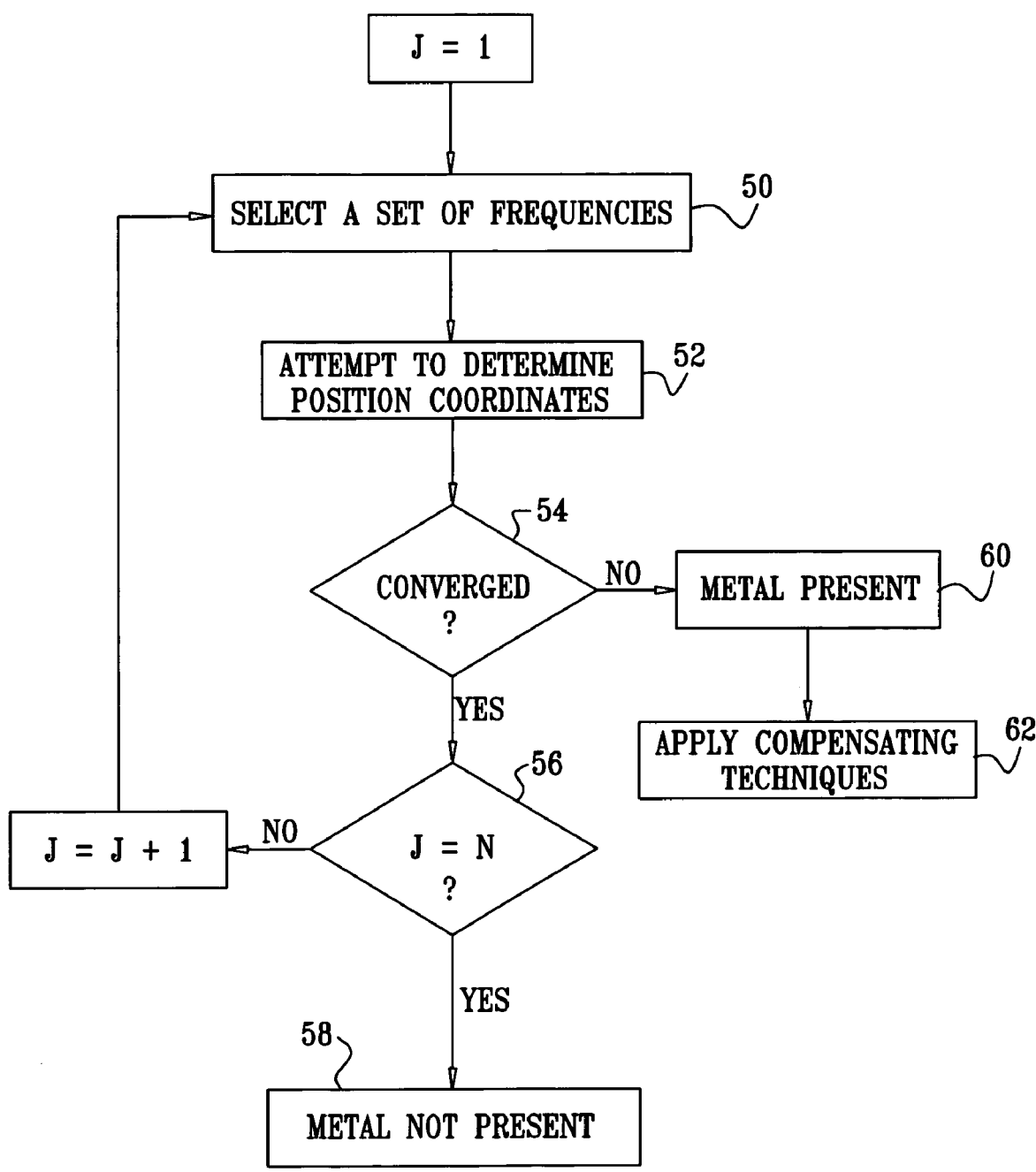

DETECTION OF METAL DISTURBANCE IN A MAGNETIC TRACKING SYSTEM

CROSS-REFERENCE TO RELATED APPLICATION

This application is related to U.S. patent application Ser. No. 09/621,322, filed Jul. 20, 2000; U.S. patent application Ser. No. 10/302,112, filed Nov. 22, 2002; U.S. patent application Ser. No. 10/448,289, filed May 29, 2003; and U.S. patent application Ser. No. 10/448,291, filed May 29, 2003. All of these related applications are assigned to the assignee of the present patent application, and their disclosures are incorporated herein by reference.

FIELD OF THE INVENTION

The present invention relates generally to non-contact tracking of objects using magnetic fields, and specifically to detecting the effect of an intruding field-responsive article in the field.

BACKGROUND OF THE INVENTION

Non-contact electromagnetic tracking systems are well known in the art, with a wide range of applications.

U.S. Pat. No. 5,391,199, to Ben-Haim, whose disclosure is incorporated herein by reference, describes a system for generating three-dimensional location information regarding a medical probe or catheter. A sensor coil is placed in the catheter and generates signals in response to externally-applied magnetic fields. The magnetic fields are generated by three radiator coils, fixed to an external reference frame in known, mutually-spaced locations. The amplitudes of the signals generated in response to each of the radiator coil fields are detected and used to compute the location of the sensor coil. Each radiator coil is typically driven by driver circuitry to generate a field at a known frequency, distinct from that of the other radiator coils, so that the signals generated by the sensor coil may be separated by frequency into components corresponding to the different radiator coils.

U.S. Patent Application Publication US 2002/0065455 A1, to Ben-Haim et al., whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils. The strengths of the signals generated in the sensor coils due to each of the different radiator coils are input to a system of non-linear algebraic equations, which are solved by numerical approximation to compute six location and orientation coordinates of the catheter.

Other locating devices using a position sensor attached to a catheter are described, for example, in U.S. Pat. No. 6,239,724 to Doron et al., U.S. Pat. No. 5,425,382 to Golden et al., U.S. Pat. No. 5,558,091 to Acker et al., U.S. Pat. No. 4,173,228 to Van Steenwyk et al., U.S. Pat. No. 5,099,845 to Besz et al., U.S. Pat. No. 5,325,873 to Hirschi et al., U.S. Pat. No. 5,913,820 to Bladen et al., U.S. Pat. No. 4,905,698 to Strohl, Jr. et al., and U.S. Pat. No. 5,425,367 to Shapiro et al. The disclosures of these patents are incorporated herein by reference. Commercial electrophysiological and physical mapping systems based on detecting the position of a probe inside the body are presently available. Among them, CARTO™, developed and marketed by Biosense Webster, Inc. (Diamond Bar, Calif.), is a system for automatic association and mapping of local electrical activity with catheter location.

The above-described tracking systems generally rely on separation of position-responsive signals into components, most typically frequency components. Each such component is assumed to correspond uniquely to a single radiator coil, in a known position, radiating a magnetic field having a regular, well-defined spatial distribution. In practice, however, when a metal or other magnetically-responsive article is brought into the vicinity of the catheter or other object being tracked, the magnetic fields in this vicinity are distorted. In a surgical environment, for example, there can be a substantial amount of conductive and permeable material, including basic and ancillary equipment (operating tables, carts, movable lamps, etc.), as well as invasive surgery apparatus (scalpels, catheters, scissors, etc.) The magnetic fields of the radiator coils may generate eddy currents in such articles, and the eddy currents then cause a parasitic magnetic field to be radiated. Such parasitic fields and other types of distortion can lead to errors in determining the position of the object being tracked.

Various methods are known in the art for detecting and compensating for the presence of magnetically-responsive articles in the field of a magnetic tracking system. For example, U.S. Pat. No. 6,147,480, to Osadchy et al., whose disclosure is incorporated herein by reference, describes a method for tracking an object using energy fields, in the presence of interference due to introduction of an article that is responsive to the fields. Energy fields are produced in the vicinity of the object, and a characteristic, such as a phase shift, of the parasitic energy fields induced due to introduction of the article is determined. This characteristic is then used in processing signals generated in response to the energy field at different locations of the object, in order to determine spatial coordinates of the object.

U.S. Pat. No. 6,373,240, to Govari, whose disclosure is incorporated herein by reference, describes an object tracking system comprising one or more sensor coils adjacent to a locatable point on an object being tracked, and one or more radiator coils, which generate alternating magnetic fields in a vicinity of the object when driven by respective alternating electrical currents. The frequencies are scanned through a plurality of values such that at any given time, each of the radiator coils radiates at a frequency which is different from the frequencies at which the other radiator coils are radiating. The sensor coils generate electrical signals responsive to the magnetic fields, which are perturbed by parasitic field components due to field-responsive articles in the vicinity of the object. The signals are analyzed to find an optimal frequency, at which the perturbing effect of the parasitic components is minimized. The optimal frequency is used in detecting spatial coordinates of the object.

U.S. Pat. No. 6,172,499, to Ashe, whose disclosure is incorporated herein by reference, describes a device for measuring the location and orientation of a receiving antenna with respect to transmitting antennas using multiple-frequency AC magnetic signals. The transmitting component consists of two or more transmitting antennas of known location and orientation relative to one another. The transmitting antennas are driven simultaneously by AC excitation, with each antenna occupying one or more unique positions in the frequency spectrum. The receiving antennas measure the transmitted AC magnetic field plus distortions caused by conductive metals. A computer then extracts the distortion component and removes it from the received signals, providing the correct position and orientation output.

U.S. Pat. No. 5,767,669, to Hansen et al., whose disclosure is incorporated herein by reference, describes a method for subtracting eddy current distortions produced in a magnetic tracking system. The system uses pulsed magnetic fields from a plurality of generators. The presence of eddy currents is detected by measuring rates of change of currents generated in sensor coils used for tracking. The eddy currents are compensated for by adjusting the duration of the magnetic pulses.

European Patent Application EP 0 964261 A2, to Dumoulin, whose disclosure is incorporated herein by reference, describes systems for compensating for eddy currents in a tracking system using alternating magnetic field generators. In a first system the eddy currents are compensated for by first calibrating the system when it is free from eddy currents, and then modifying the fields generated when the eddy currents are detected. In a second system the eddy currents are nullified by using one or more shielding coils placed near the generators.

U.S. Pat. No. 6,369,564, to Khalfin et al., whose disclosure is incorporated herein by reference, describes an electromagnetic tracking system that includes at least one source of an AC electromagnetic field, at least one witness sensor measuring components of the electromagnetic induction vector at known spatial points close to or within the volume of interest, and at least one wireless probe sensor placed on the object being tracked. The signal generated by the witness sensors is used in separating environmental distortion signals from the probe sensor signal, by distinguishing the phase of the signal from the probe sensor.

SUMMARY OF THE INVENTION

Embodiments of the present invention provide methods for enhancing the accuracy of an electromagnetic tracking system, by detecting the presence and effect of field-responsive articles, such as metal tools, in the vicinity of the object being tracked. Such systems typically comprise one or more radiator coils, which produce energy fields in the vicinity of the object. One or more sensor coils generate signals that are indicative of spatial coordinates of the object. A system controller analyzes the signals in order to compute the object coordinates by fitting the signal amplitudes to a mathematical model of the energy fields produced by the radiator coils.

When the fields are perturbed by an article in the detection volume, the mathematical model is no longer precisely correct, and the computation of the coordinates may therefore fail to converge. The perturbation of the fields by the article, however, is typically dependent on the frequencies of the fields. Consequently, the coordinate computation may still converge at some frequencies despite the perturbation (and may yield an inaccurate result). To address this problem, in embodiments of the present invention, each of the radiator coils is driven to radiate at multiple different frequencies, and the computation of the coordinates of the object is repeated for each of the different frequencies. If any of these computations fail to converge, the controller may conclude that the fields have been perturbed by a field-responsive article in the detection volume. The controller may then take steps to correct the computed coordinates, or at least to alert a user of the system as to the possible loss of coordinate accuracy.

There is therefore provided, in accordance with an embodiment of the present invention, a method for tracking an object, including:

producing energy fields at a plurality of different frequencies in a vicinity of the object;

receiving signals that are generated at a location of the object at the different frequencies in response to the energy fields;

making multiple computations of spatial coordinates of the object based on the signals received at the different frequencies; and ascertaining whether the energy fields have been perturbed by an article in the vicinity of the object by testing a convergence of the computations.

In a disclosed embodiment, producing the energy fields includes producing magnetic fields, and receiving the signals includes receiving electrical signals which are generated responsively to the magnetic fields. Typically, producing the magnetic fields includes driving multiple radiator coils with electrical currents at the different frequencies so as to generate the magnetic fields, wherein driving the multiple radiator coils includes driving each of the coils to generate the magnetic fields at a unique, respective set of the frequencies. Additionally or alternatively, receiving the electrical signals includes receiving the electrical signals from one or more sensor coils that are fixed to the object.

In one embodiment, producing the energy fields includes scanning sequentially through a predetermined sequence of the frequencies. In another embodiment, producing the energy fields includes generating the fields simultaneously at the different frequencies.

Typically, making the multiple computations includes solving a set of simultaneous equations relating the received signals to the spatial coordinates of the object. Additionally or alternatively, making the multiple computations includes applying an iterative method of approximation to determine the spatial coordinates, and testing the convergence includes evaluating a convergence criterion of the iterative method. Testing the convergence may include detecting a discrepancy between the spatial coordinates computed at the different frequencies.

Optionally, the method includes, upon ascertaining that the energy fields have been perturbed, correcting the computations to compensate for a presence of the article in the vicinity of the object.

There is also provided, in accordance with an embodiment of the present invention, apparatus for tracking an object, including:

at least one radiator, which is adapted to produce energy fields at a plurality of different frequencies in a vicinity of the object;

at least one sensor, fixed to the object, which is adapted to generate signals in response to the energy fields at the different frequencies; and a system controller, which is adapted to make multiple computations of spatial coordinates of the object based on the signals generated at the different frequencies, and to ascertain whether the energy fields have been perturbed by an article in the vicinity of the object by testing a convergence of the computations.

The present invention will be more fully understood from the following detailed description of the embodiments thereof, taken together with the drawings in which:

BRIEF DESCRIPTION OF THE DRAWINGS

FIG. 2 is a flow chart that schematically illustrates a method for detecting the presence of a field-disturbing article in an object tracking system, in accordance with an embodiment of the present invention.

DETAILED DESCRIPTION OF EMBODIMENTS

Figure 1:
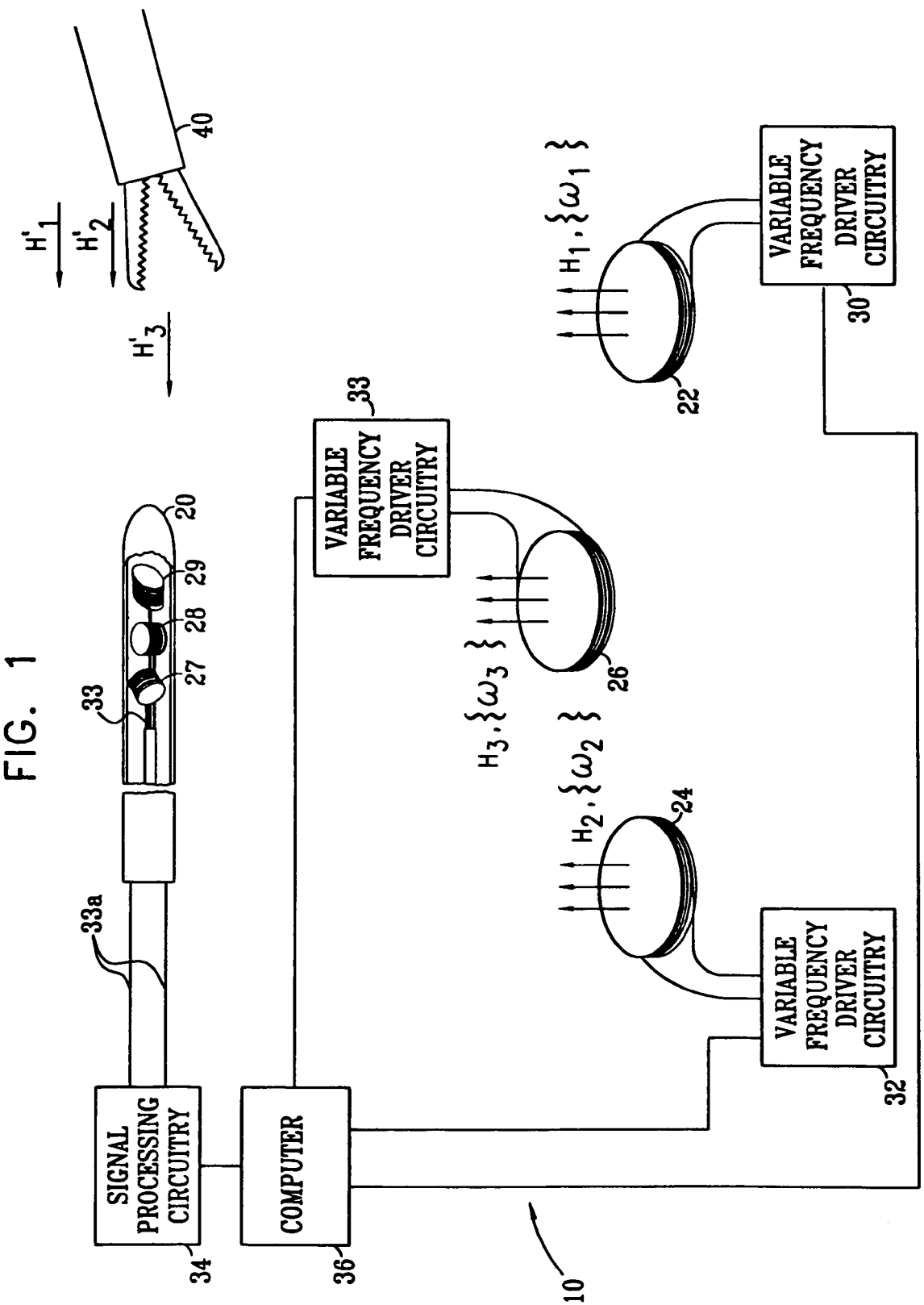
FIG. 1 is a schematic, pictorial illustration showing a system for tracking coordinates of a probe, in accordance with an embodiment of the present invention.

Reference is now made to FIG. 1, which schematically illustrates a system 10 for tracking a probe 20, such as a catheter for medical use, in accordance with an embodiment of the present invention. Similar systems are described in the above-mentioned U.S. Pat. Nos. 5,319,199, 6,147,480 and 6,373,240 and Patent Publication US 2002/0065455 A1. Elements of the description are repeated here for the sake of clarity and completeness.

System 10 comprises a plurality of radiator coils 22, 24 and 26, which are placed in known positions and orientations. The radiator coils are driven by variable-frequency driver circuits 30, 32 and 33 to generate respective magnetic fields $\vec{H}_1$, $\vec{H}_2$ and $\vec{H}_3$, at respective sets of frequencies $\{\omega_1\}$, $\{\omega_2\}$ and $\{\omega_3\}$, in the vicinity of probe 20. Typically, sets $\{\omega_1\}$, $\{\omega_2\}$ and $\{\omega_3\}$ comprise frequencies in the approximate range of 100 Hz-20 kHz, although higher and lower frequencies may also be used. The sets of frequencies $\{\omega_1\}$, $\{\omega_2\}$ and $\{\omega_3\}$ at which the coils radiate are set by a computer 36, which serves as the system controller for system 10. The sets of frequencies $\{\omega_1\}$, $\{\omega_2\}$ and $\{\omega_3\}$ may all include the same frequencies or different frequencies. In any case, computer 36 controls circuits 30, 32 and 33 according to a known multiplexing pattern, which provides that at any point in time, no more than one radiator coil is radiating at any given frequency. Typically, each driver circuit is controlled to scan cyclically over time through the frequencies in its respective set. Alternatively, each driver circuit may drive the respective coil 22, 24 or 26 to radiate at multiple frequencies simultaneously.

For the purposes of system 10, radiator coils 22, 24 and 26 may be arranged in any convenient position and orientation, so long as they are fixed in respect to some reference frame, and so long as they are non-overlapping, that is, there are no two radiator coils with the exact, identical location, i.e. position and orientation. It should be understood that placement of the radiator coils, as well as their size and shape, will vary according to the application of the invention. Typically, for a medical application, the radiator coils comprise wound annular coils from about 2 to 20 cm in outer diameter (O.D.) and from about 0.5 to 2 cm thick, in a coplanar, triangular arrangement, wherein the centers of the coils are from about 2 to 30 cm apart. Bar-shaped transmitters or even triangular or square-shaped coils could also be useful for such medical applications. When a prone patient is to be the subject of a procedure involving the instant invention, the radiator coils may be positioned in or below the surface upon which the patient is resting (such as an operating table), below the portion of the patient's body in which the procedure is to be performed. In other applications, the radiator coils may be near or in contact with the skin of the patient.

Probe 20 includes sensor coils 27, 28 and 29, which generate electrical current signals in response to the magnetic fields produced by the radiator coils. The sensor coils may be wound on either air cores or a core of material. In the embodiment shown in FIG. 1, the sensor coils have mutually orthogonal axes, one of which is conveniently aligned with the long longitudinal axis of probe 20. Unlike prior art position sensors (used for other applications), which contain three coils that are concentrically located, or at least whose axes intercept, the coils in this embodiment are closely spaced along the longitudinal axis of the probe to reduce the diameter of the probe and leave space for other elements, such as a working channel (not shown).

At any instant in time, the signals generated by sensor coils 27, 28 and 29 comprise components of the specific frequencies in sets $\{\omega_1\}$, $\{\omega_2\}$ and $\{\omega_3\}$ being generated by the radiator coils. The respective amplitudes of these signals are dependent on the position and orientation of probe 20 relative to the positions and orientations of the radiator coils. The signals generated by sensor coils 27, 28 and 29 are conveyed via leads 33a to the proximal end of the probe, for processing by signal processing circuitry 34. Leads b 33a typically comprise twisted pairs to reduce pick-up and may be further electrically shielded. The processed sensor signals are then used by computer 36, together with a representation of the signals used to drive radiator coils 22, 24 and 26, to calculate position and orientation coordinates of probe 20.

In one embodiment of the invention, sensor coils 27, 28, 29 have an inner diameter of about 0.5 mm and have 800 turns of 16 μm diameter wire to give an overall coil diameter of 1-1.2 mm. The effective capture area of the coil is then about 400 mm². It will be understood that these dimensions may vary over a considerable range and are only representative of an exemplary range of dimensions. In particular, the size of the sensor coils can be as small as 0.3 mm (with some loss of sensitivity) or as large as 2 mm or more. The wire size of the sensor coils can range from 10-31 μm, and the number of turns between 300 and 2600, depending on the maximum allowable size and the wire diameter. The effective capture area of the sensor coils is typically made as large as feasible, consistent with the overall size requirements. While coils 27, 28 and 29 are shown as being cylindrical, other shapes can also be used. For example, barrel-shaped, square or other shaped coils may be useful, depending on the geometry of probe 20.

Although in FIG. 1, system 10 is shown as comprising three radiator coils and three sensor coils, in other embodiments of the present invention, different numbers, types and configurations of radiators and sensors may used. A fixed frame of reference may be established, for example, using only two non-overlapping radiator coils to generate distinguishable magnetic fields. Two non-parallel sensor coils may be used to measure the magnetic field flux due to the radiator coils, in order to determine six position and orientation coordinates (X, Y, Z directions and pitch, yaw and roll orientations) of the distal end of probe 20. Using three radiator coils and three sensor coils, however, tends to improve the accuracy and reliability of the position measurement.

Alternatively, if only a single sensor coil is used, computer 36 can still determine five position and orientation coordinates (X, Y, Z directions and pitch and yaw orientations). Specific features and functions of a single coil system (also referred to as a single axis system) are described in U.S. Pat. No. 6,484,118, whose disclosure is incorporated herein by reference.

To determine the coordinates of probe 20, computer fits the probe signals to a mathematical model of the magnetic fields generated by radiator coils 22, 24 and 26. This computation is performed multiple times at each probe location, as described hereinbelow, using a different group of radiator frequencies $\{\omega_1, \omega_2, \omega_3\}$ in each computation. The form of the computation, for three radiator coils and three sensor coils as shown in FIG. 1, is given in the above-mentioned Patent Publication US 2002/0065455 A1 as a system of nine non-linear algebraic equations:

$$(-F_{S,C}(x, y, z, \epsilon, \xi, \zeta)=B_{S,C}(\omega_C)|_{S=1,2,3})_{C=1,2,3} \quad (1)$$

Here $B_{S,C}(\omega_C)$ represents the actual signal received from sensor coil s at the unknown location and orientation coordinates (x, y, z, $\epsilon$, $\xi$, $\zeta$, due to the field of radiator coil c, while the radiator coil was driven at frequency $\omega_C$ in set $\{\omega_C\}$. $F_{S,C}(x, y, z, \epsilon, \xi, \zeta)$ represents the signal that would be received from the sensor coils at these coordinates, given a known model of the magnetic fields generated by the radiator coils. This model depends on the specific locations and geometry of radiator coils 22, 24 and 26, as is known in the art.

Assuming that there are no articles in the vicinity of probe 20 that significantly perturb the fields generated by the radiator coils, $F_{S,C}$ at any given location is uniquely determined by the driving currents and the known locations and orientations of the radiator coils:

$$B_S(t) = \sum_C B_{S,C}(t) = \sum_C A_C \sin(\omega_C t + \phi_C) \quad (2)$$

Here $A_C$ and $\Phi_C$ are the amplitude and phase of the position signal component at frequency $\omega_C$. The system of equations represented by equations (1) and (2) is typically solved using numerical approximation methods known in the art, such as the Newton-Raphson method or multidimensional secant methods, in order to determine coordinates (x, y, z, $\epsilon$, $\xi$, $\zeta$). The computation is expected to converge uniquely to the correct coordinate values, regardless of the radiator coil frequencies $\omega_C$ that are used.

As illustrated in FIG. 1, however, this expectation may not be realized when a metal or other magnetic field-responsive article, such as a surgical tool 40, is introduced into the vicinity of probe 20. Tool 40 generally receives energy from unperturbed fields $\vec{H}_1$, $\vec{H}_2$ and $\vec{H}_3$, and re-radiates perturbing, parasitic magnetic fields, $\vec{H}_1'$, $\vec{H}_2'$ and $\vec{H}_3'$, at the specific frequencies from sets $\{\omega_1\}$, $\{\omega_2\}$ and $\{\omega_3\}$ that are being generated by the radiator coils. The phases and amplitudes of the parasitic fields generally depend on properties of tool 40, including its dielectric constant, magnetic permeability, geometrical shape and orientation relative to the radiator coils. The phases and amplitudes of the parasitic fields are also a function of the specific frequencies of fields $\vec{H}_1$, $\vec{H}_2$ and $\vec{H}_3$. Therefore, the model of the unperturbed magnetic fields generated by radiator coils 22, 24 and 26 no longer corresponds precisely to the actual fields that will be encountered by sensor coils 27, 28 and 29. Rather, the signals generated by the sensor coils now include a parasitic component:

$$B_S(t) = \sum_C B_{S,C}(t) = \sum_C A_C \sin(\omega_C t + \phi_C) + A_C' \sin(\omega_C t + \phi_C') \quad (3)$$

wherein $A_C'$ and $\phi_C'$ are the amplitude and phase of the parasitic signal component at frequency $\omega_C$.

As a result of these parasitic effects, when equation (1) is solved, it may give different results for different choices of radiator frequencies. Furthermore, if the perturbation is severe at certain frequencies, the approximation method used to solve the system of equations may fail to converge at all.

Although system 10 is shown to comprise three radiator coils and three sensor coils, similar problems of field perturbation arise when different types of antennas are used for field generation and reception, as well as when larger or smaller numbers of field generators and receivers are used. For instance, coils 27, 28 and 29 in probe 20 may be used as the field generators, while external coils 22, 24 and 26 are used as receivers. As another example, noted above, the tracking system may comprises only a single sensor coil and multiple radiator coils, or a single radiator coil and multiple sensor coils. The use of a single sensor coil with multiple radiator coils is described, for example, in the above-mentioned U.S. patent application Ser. No. 09/621,322 and U.S. Pat. No. 6,484,118. This application details a number of estimation methods for determining the coordinates of a probe containing a single sensor coil, including a steepest-descent technique and a global estimation technique. Regardless of the choice of technique, field perturbation by field-responsive articles in the single-sensor system may likewise cause coordinate computations at different frequencies to converge to different values or to fail to converge at all.

FIG. 2 is a flow chart that schematically illustrates a method carried out by computer 36 to detect the presence of a field-disturbing article, such as tool 40, in the vicinity of probe 20, in accordance with an embodiment of the present invention. As noted above, although this method is described specifically with reference to system 10, it is similarly applicable to magnetic tracking systems of other types and configurations. To begin the method, the control unit selects a first set of one or more frequencies for radiator coils 22, 24 and 26 at a frequency selection step 50. If all of the radiator coils operate at the same frequency (using time-domain multiplexing, for example, to distinguish the fields generated by the different radiator coils), the set of frequencies selected at this step contains only a single frequency. Alternatively, in systems in which the respective fields generated by the radiator coils have different frequencies, the set of frequencies selected at this step typically comprises a frequency selected from each of sets $\{\omega_1\}$, $\{\omega_2\}$ and $\{\omega_3\}$. Furthermore, each of the radiator coils may be driven at multiple frequencies simultaneously.

Radiator coils 22, 24 and 26 generate magnetic fields at the selected frequency or respective frequencies, and responsive to the fields, sensor coils 27, 28 and 29 generate position signals. Computer 36 then attempts to determine the position and orientation of probe 20 by solving the set of simultaneous equations represented by equation (1) and (2), using the position signal amplitudes as inputs $B_{S,C}(\omega_C)$, at a position determination step 52. When one or more of the radiator coils generate fields at multiple different frequencies simultaneously, computer 36 typically uses time- or frequency-domain filtering techniques to separate the signal components at the different radiator frequencies before solving the simultaneous equations. Any suitable method may be used to solve the equations, such the methods described above or other methods known in the art.

Computer 36 tests whether the computation has converged to a satisfactory solution, at a convergence check step 54. As long as the computation converges, the computer concludes tentatively that the radiator fields have not been significantly perturbed by any interfering article. In such a case, the computer returns to step 50, selects a different set of frequencies, and then repeats steps 52 and 54. At each pass through step 54, the computer checks the convergence to ascertain both that:

The computation of the probe coordinates at the current set of radiator frequencies has itself converged, i.e., that after a certain number of iterations through whatever fitting method is used, the variation of the computed coordinates from iteration to iteration is within a predetermined error bound; and The probe coordinates computed at the current set of radiator frequencies is within a predetermined error bound, typically about 3 mm, of the coordinates computed in previous passes through steps 50-54, using different frequency sets.

The loop through steps 50-54 repeats N times, wherein, for example, N may equal 5 or 10. Computer 36 checks for completion of all N repetitions, at a completion check step 56. If convergence occurs all N times, the computer determines that there is no significant field perturbation due to metal tool 40 (or any other field-perturbing article), at a negative determination step 58.

On the other hand, if it is determined at any of the iterations through step 54 that the coordinate computation has failed to converge, according to the criteria defined above, computer 36 concludes that a field-perturbing article is present, at a positive determination step 60. This determination can be made because the presence of such an article is the only reasonably-expected cause (other than a mechanical or electrical failure) for the equations not to converge. Once the determination has been made, the computer may apply compensating techniques to correct the coordinate computation for the perturbation caused by the interfering article, at a compensation step 62. For example, the techniques described in the above-mentioned U.S. Pat. Nos. 6,147,480 and 6,373,240 may be used for this purpose, as may other techniques known in the art. Additionally or alternatively, computer 36 may notify the user of system 10 that the current coordinates of probe 20 are suspect and should be used with caution until, for example, tool 40 has been removed from the vicinity of the probe. If the compensating techniques do not resolve the problem of non-convergence, computer 36 may notify the user of a system failure.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for tracking an object, comprising:
   (i) producing energy fields at a plurality of different frequencies in a vicinity of the object;
   (ii) receiving signals that are generated at a location of the object at the different frequencies in response to the energy fields;
   (iii) making multiple computations of spatial coordinates of the object based on the signals received at the different frequencies; ascertaining whether the energy fields have been perturbed by an article in the vicinity of the object by testing a convergence of the computations; and
   (iv) if testing reveals a convergence of the computations then repeating steps (i) through (iv) for N repetitions, wherein N equals a plurality of times.

2. The method according to claim 1, wherein producing the energy fields comprises producing magnetic fields, and wherein receiving the signals comprises receiving electrical signals which are generated responsively to the magnetic fields.

3. The method according to claim 2, wherein producing the magnetic fields comprises driving multiple radiator coils with electrical currents at the different frequencies so as to generate the magnetic fields.

4. The method according to claim 3, wherein driving the multiple radiator coils comprises driving each of the coils to generate the magnetic fields at a unique, respective set of the frequencies.

5. The method according to claim 3, wherein receiving the electrical signals comprises receiving the electrical signals from one or more sensor coils that are fixed to the object.

6. The method according to claim 1, wherein producing the energy fields comprises scanning sequentially through a predetermined sequence of the frequencies.

7. The method according to claim 1, wherein producing the energy fields comprises generating the fields simultaneously at the different frequencies.

8. The method according to claim 1, wherein making the multiple computations comprises solving a set of simultaneous equations relating the received signals to the spatial coordinates of the object.

9. The method according to claim 1, wherein making the multiple computations comprises applying an iterative method of approximation to determine the spatial coordinates, and wherein testing the convergence comprises evaluating a convergence criterion of the iterative method.

10. The method according to claim 1, wherein testing the convergence comprises detecting a discrepancy between the spatial coordinates computed at the different frequencies.

11. The method according to claim 1, and comprising, upon ascertaining that the energy fields have been perturbed, correcting the computations to compensate for a presence of the article in the vicinity of the object.

12. Apparatus for tracking an object, comprising:
    at least one radiator, which is adapted to produce energy fields at a plurality of different frequencies in a vicinity of the object;
    at least one sensor, fixed to the object, which is adapted to generate signals in response to the energy fields at the different frequencies; and
    a system controller, which is adapted to: (i) make multiple computations of spatial coordinates of the object based on the signals generated at the different frequencies, and to (ii) ascertain whether the energy fields have been perturbed by an article in the vicinity of the object by testing a convergence of the computations, wherein the system controller repeats (i) and (ii) when testing reveals a convergence of the computations for N repetitions, wherein N equals a plurality of times.

13. The apparatus according to claim 12, wherein the energy fields comprise magnetic fields, and wherein the signals comprise electrical signals which are generated by the at least one sensor responsively to the magnetic fields.

14. The apparatus according to claim 13, wherein the at least one radiator comprises multiple radiator coils and driving circuitry, which is adapted to drive the radiator coils with electrical currents at the different frequencies so as to generate the magnetic fields.

15. The apparatus according to claim 14, wherein the driving circuitry is adapted to drive each of the coils to generate the magnetic fields at a unique, respective sequence of the frequencies.

16. The apparatus according to claim 14, wherein the at least one sensor comprises one or more sensor coils.

17. The apparatus according to claim 12, wherein the at least one radiator is adapted to generate the energy fields sequentially with a predetermined sequence of the frequencies.

18. The apparatus according to claim 12, wherein the at least one radiator is adapted to generate the fields simultaneously at the different frequencies.

19. The apparatus according to claim 12, wherein the system controller is adapted to compute the spatial coordinates by solving a set of simultaneous equations relating the signals to the spatial coordinates of the object.

20. The apparatus according to claim 12, wherein the system controller is adapted to compute the spatial coordinates by applying an iterative method of approximation, and to test the convergence of the computations by evaluating a convergence criterion of the iterative method.

21. The apparatus according to claim 12, wherein the system controller is adapted to test the convergence by detecting a discrepancy between the spatial coordinates computed at the different frequencies.

22. The apparatus according to claim 12, wherein the system controller is adapted, upon ascertaining that the energy fields have been perturbed, to correct the computations to compensate for a presence of the article in the vicinity of the object.

* * * * *